United States Patent [19]

Ratton

[11] Patent Number: 5,369,976

[45] Date of Patent: Dec. 6, 1994

[54] METHOD AND APPARATUS FOR MEASURING EVAPORATIVE VEHICLE EMISSIONS IN A FIXED-VOLUME/VARIABLE TEMPERATURE TEST CHAMBER

[75] Inventor: Kenneth Ratton, Farmington Hills, Mich.

[73] Assignee: Power-Tek, Inc., Farmington Hills, Mich.

[21] Appl. No.: 53,086

[22] Filed: Apr. 26, 1993

[51] Int. Cl.$^5$ .................................... G01M 19/00
[52] U.S. Cl. ................................ 73/23.2; 73/116
[58] Field of Search .............. 73/118.1, 23.35, 23.2, 73/116, 23.31, 40, 49.7

[56] References Cited

U.S. PATENT DOCUMENTS

| | | | |
|---|---|---|---|
| 3,942,357 | 3/1976 | Jenkins | 73/23.2 X |
| 4,847,790 | 7/1989 | Suzuki et al. | 364/558 X |
| 5,214,957 | 6/1993 | Collins | 73/40 |

*Primary Examiner*—Hezron E. Williams
*Assistant Examiner*—James M. Olsen
*Attorney, Agent, or Firm*—Brooks & Kushman

[57] ABSTRACT

Provided is a method and apparatus for measuring evaporative vehicle emissions in a fixed-volume/variable temperature test chamber. The method comprises the steps of providing a volume compensation device in fluid communication with a test chamber for compensating for changes in the test chamber fluid volume, determining the density of the evaporative emissions and the test chamber fluid in mass per unit volume at selected sample times $t_n$, where n is a positive integer, measuring the temperature of the test chamber fluid at the sample times $t_n$, measuring the absolute fluid pressure of fluid at the sample times $t_n$, determining the difference in the test chamber fluid volume between successive sample times $t_n$, determining the mass of the evaporative emissions in lost volume and mass measurements and summing the determined masses of the evaporative emissions to provide a calculation of the evaporative emissions lost by the volume compensation device during expansion of the test chamber fluid and summing this with the final sample to determine the total evaporative emissions from a vehicle. In an alternative embodiment, a plurality of impingers are also provided for use in determining the lost mass of alcohol emissions in flexible fueled vehicles.

2 Claims, 4 Drawing Sheets

METHOD AND APPARATUS FOR MEASURING EVAPORATIVE VEHICLE EMISSIONS IN A FIXED-VOLUME/VARIABLE TEMPERATURE TEST CHAMBER

TECHNICAL FIELD

This invention relates generally to sealed housings for evaporative determination. More specifically, this; invention relates to a method and apparatus for measuring evaporative vehicle emissions in a fixed-volume/variable temperature test chamber.

BACKGROUND OF THE INVENTION

As used in the art, the acronym "SHED" generally refers to sealed housings for evaporative determination. These SHEDS are generally rectangular enclosures which define fluid-fillable test chambers adapted to measure evaporative emissions such as hydrocarbon from automobiles, trucks and other motor vehicles. Historically, such testing was performed while the test chamber fluid (typically air) was maintained at a constant temperature. In operation, the test vehicle was placed in the SHED with the engine and all other equipment turned off. The door to the SHED was then closed and sealed. Thereafter, selected emissions such as hydrocarbon (HC) were measured at the beginning and end of a fixed timed period which was generally one hour. The SHED test is one step of the federal test procedure which is described in the Federal Register, subpart B, 86,101 to 86.145-82.

Those skilled in the art will recognize that recent proposed regulations developed for the Clean Air Act have revised the evaporative portion of the federal test procedure. As revised, the evaporative portion now requires the use of a variable-volume/variable-temperature test chamber. As more thoroughly described in a draft Evaporative Regulations OMB1 of Nov. 18, 1992, Sec. 86,078-3 to 86.098-10, new SHEDS must therefore define fluid-fillable test chambers capable of changing fluid temperature following prescribed fluid temperature profiles.

It should be noted that sealing technology, which was not a significant issue under the prior art constant temperature systems, has now become a complex problem for SHED designers under the variable temperature requirements. As those skilled in the art will recognize, by design, conventional SHEDs must include a plurality of penetrations for sample ports and temperature probes; as well as a vehicle entrance/exit door, an operator egress door and a purge vent. All of these doors and penetrations must be sufficiently sealed or leakage will occur and emission sample will be lost. Because of the new variable temperature requirements and the need for a sealed housing to prevent loss of emissions, the corresponding volume compensation requirement was introduced to avoid pressurizing the SHED.

To comply with the new volume compensation requirements, conventional SHEDs have incorporated various volume control devices for varying the volume of the fluid-fillable test chambers during expansion and contraction of test chamber fluid. Typically, such devices have been provided in fluid communication with the fluid (typically air) outside of the test chamber and are controlled by pure pressure feedback systems through the use of differential pressure transducers. Typical volume compensation devices include, for example, a plurality of inflatable bags which are disposed on the internal walls of the test chamber. During expansion of the test chamber fluid, the bags are deflated to increase the volume of the test chamber. Similarly, during contraction cycles, the bags are inflated to decrease the volume of the test chamber. It should be noted, however, that because these devices use differential pressure transducers as feedback, a near-perfect seal is required for the SHED to operate properly. Indeed, induced pressure variations, however slight, will bias the differential pressure transducer and cause an error in the amount of volume compensation. The resulting error will be magnified by forcing the sample out of the SHED or diluting the sample by drawing fluid into the SHED. Because truly "sealed" housings are nearly impossible to achieve, the pressure control systems of the prior art have proven unreliable and thus highly susceptible to error.

As those skilled in the art will recognize, the need for perfect sealing arises only because of the fear of emission sample Loss. Thus, if a control system could be designed to precisely calculate emission loss, a fixed-volume test chamber could be utilized and SHED pressurization could be obviated by merely providing or evacuating fluid directly from the SHED test chamber.

DISCLOSURE OF INVENTION

It is an object of the present invention to overcome the limitations of the prior art by providing a leak-tolerant apparatus and method for measuring evaporative vehicle emissions in a fixed-volume test chamber subject to prescribed fluid temperature profiles.

In accordance with the invention, there is provided a housing having an interior portion defining a fixed volume fluid-fillable test chamber and an exterior portion. A fluid temperature sensor and a fluid pressure sensor are provided in thermal communication with the test chamber fluid. Fluid conditioning means is also provided in fluid communication with the test chamber for controlling the temperature of the test chamber fluid. There is also provided flow metering means such as a mass flow meter or positive displacement pump in fluid communication with the test chamber for compensating for changes in test chamber fluid volume. Finally, there is provided control means in electrical communication with the fluid temperature sensor, the fluid pressure sensor and the fluid metering means for determining the total mass of evaporative emissions lost during expansion of the test chamber fluid in accordance with the Ideal Gas Law ($PV = nRT$). In an alternative embodiment, a plurality of impingers are also provided for use in determining the lost mass of alcohol emissions in flexible fueled vehicles.

Also, in accordance with the invention, there is provided a method of measuring evaporative emissions emitted from motor vehicles in accordance with prescribed fluid temperature profiles in a fixed-volume test chamber filled with a fluid having a predetermined mass, volume, temperature and pressure at time $t_0$. The claimed method comprises the steps of providing volume compensation means in fluid communication with the test chamber for compensating for changes in test chamber fluid volume. Thereafter, the density of evaporative emissions in the test chamber fluid must be determined in mass per unit volume at selected sample times $t_n$, where n is a positive integer. Also at time $t_n$, the temperature of the test chamber fluid must be measured along with the absolute fluid pressure of the test chamber fluid. Thereafter, for positive changes in volume, the mass volume and therefore densities of the sample at each time $t_n$ may be determined. The density of the sample at time $t_n$ is averaged with the density of the previous sample and multiplied by the change in volume over the same time period. The result is summed with subsequent results to provide a calculation of the sample lost by the volume compensation means during expansion of the test chamber fluid. This loss calculation summed with the final determined sample mass will result in the total evaporative emissions from the vehicle.

In the alternative embodiment referenced above, three (3) impingers are utilized to determine the alcohol concentration of the test chamber fluid during three corresponding time periods i.e. at the start of the test, throughout the test and at the completion of the test. By subtracting the determined alcohol concentration at the beginning of the test from the determined concentration at the end of the test, the mass of alcohols emitted may be calculated. This mass, added to the mass emitted during the test (the mass trapped in the second impinger) yields the total evaporated alcohol emissions during the test.

The above objects and other objects, features, and advantages of the present invention are readily apparent from the following detailed description of the preferred embodiments of the invention when taken in connection with the accompanying drawings.

BEST MODES FOR CARRYING OUT THE INVENTION

Figure 1:
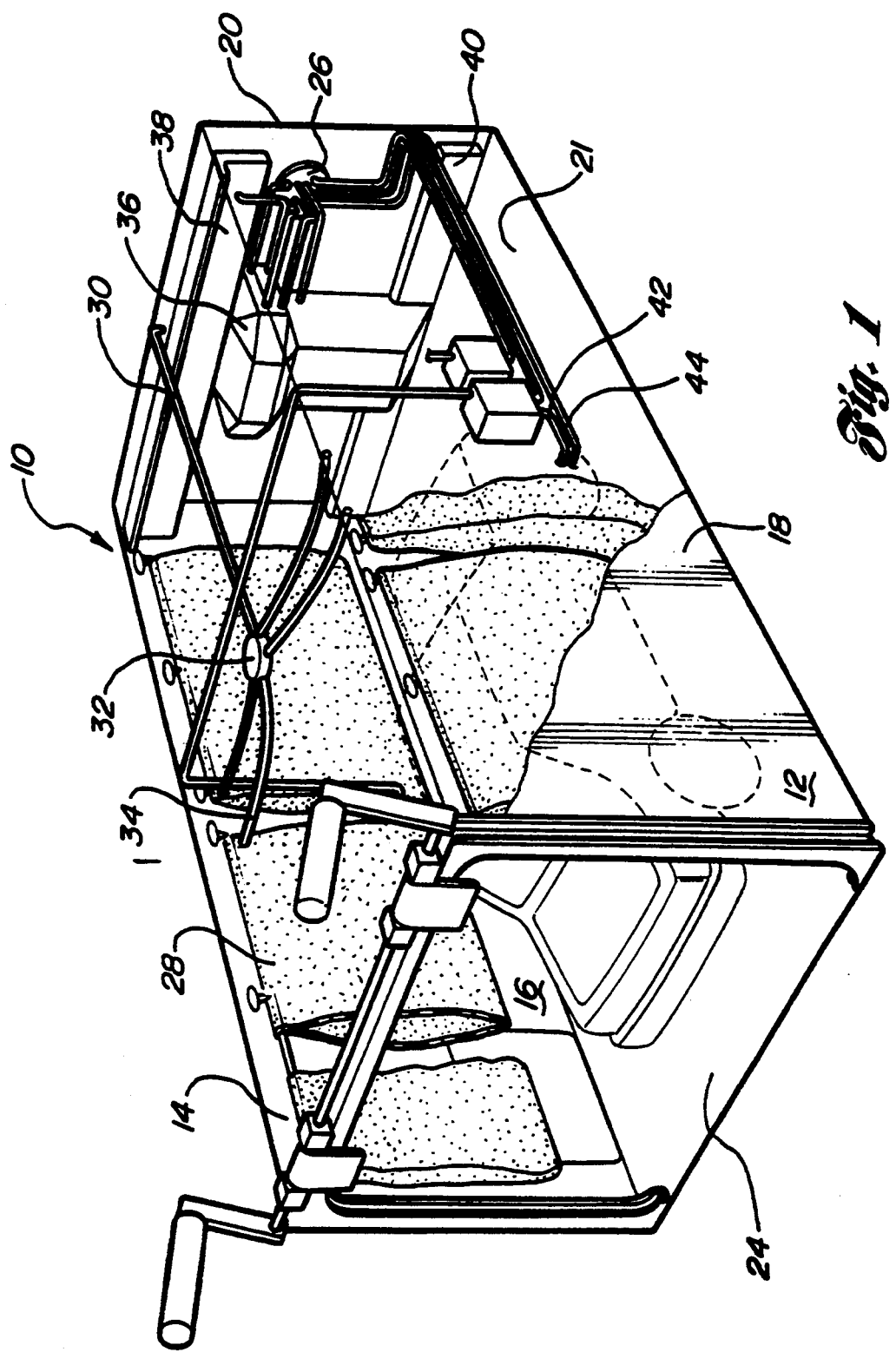
FIG. 1 is a perspective view of a prior art vehicle test chamber.

Referring to FIG. 1, a prior art variable-volume Sealed Housing For Evaporative Determination (SHED) is shown generally indicated by reference numeral 10. SHED 10 is a generally rectangular enclosure having a bottom portion 12, a top portion 14, side portions 16 and 18 and a rear portion 20. A vehicle entrance/exit door 22 is also provided to define a fluid-fillable test chamber 21. SHED 10 further includes an operator egress door 24 and a plurality of penetrations 26 for sample ports, temperature probes and the like. Still further, prior art SHED 10 includes a plurality of air-expandable and partially air-filled bags 28 provided in fluid communication with an external pumping means (not shown) through tubing 30, manifold 32 and branch tubing 34.

Still referring to FIG. 1, there is shown a heating, and cooling means 36 in fluid communication with air supply plenum 38 and return air plenum 40. SHED 10 further includes a pair of resistive temperature devices (RTD's) one of which is shown and designated by reference numeral 42. As seen, bags 28 serve the variable-volume requirement and have historically been controlled through the use of pure pressure feedback control systems which determine the differential pressure between the test chamber fluid and the fluid outside of SHED 10. In operation, bags 28 are inflated or deflated so as to decrease or increase the test chamber volume accordingly.

Figure 2:
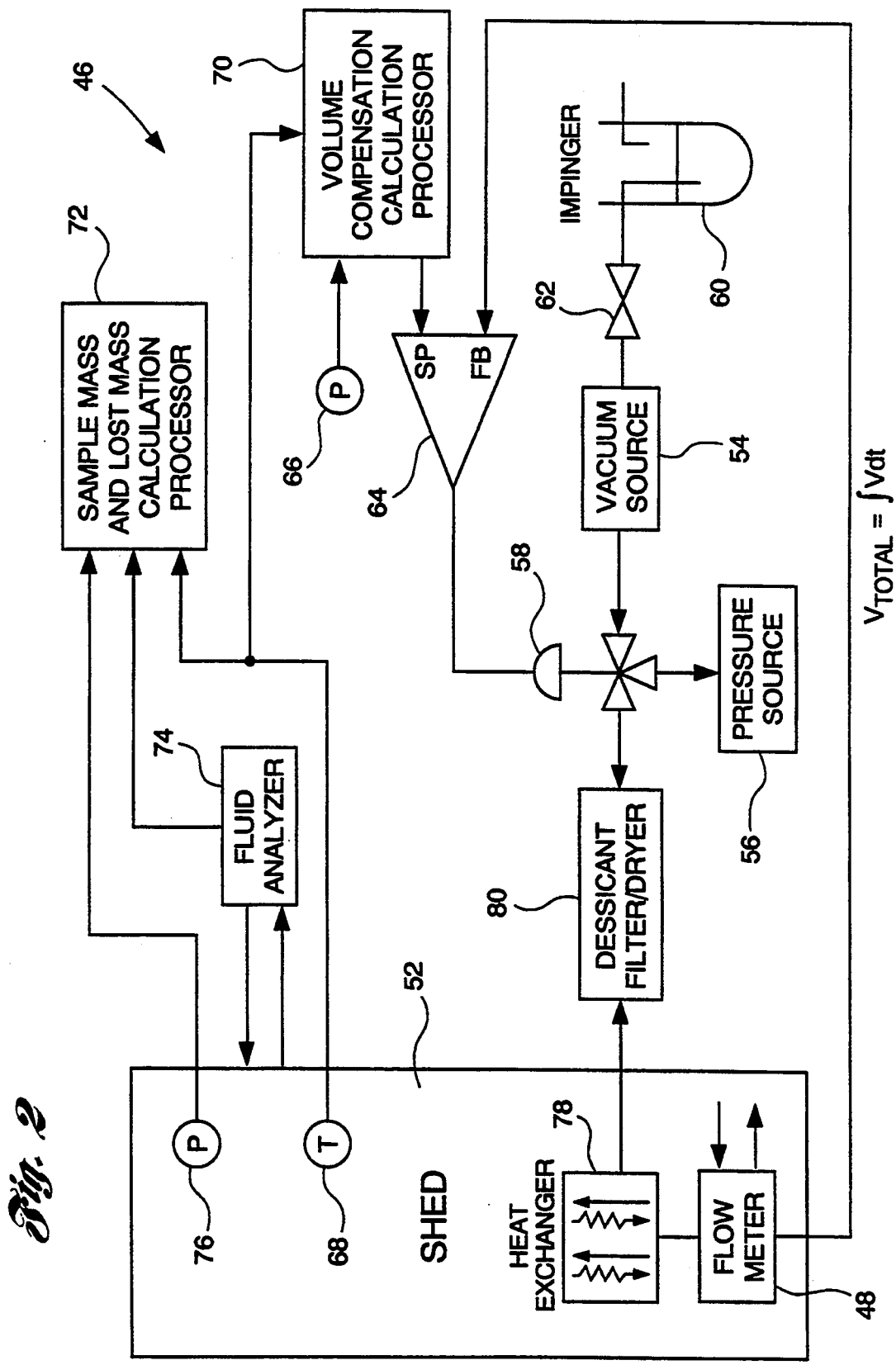
FIG. 2 is a schematic diagram of the control system of the present invention.

Turning now to FIG. 2, there is shown a schematic diagram of the control system of the present invention designated generally by reference numeral 46. As seen, in the preferred embodiment, control system 46 includes a flow metering device 48 which is provided in fluid communication with test chamber 52. Flow metering device 48 is further provided in fluid communication with a vacuum source 54 for evacuating fluid from test chamber 52 during expansion cycles. Similarly, flow metering device 48 is provided in fluid communication with a pressure source such as pump 56 which is preferably a filtered or zero air source for providing filtered fluid, free from selected contaminants (i.e. at least the constituents sought to be measured) to the test chamber during contraction cycles. As seen, flow metering device 48 is used as feedback for the volume compensation loop. As the air in test chamber 52 changes temperature, the volume compensation calculation will determine the total change in volume of the test chamber air. This calculated number compared to the total volume of air measured by flow metering device 48 to have been drawn in or expelled from test chamber 52 will be compared and a correction will be made in the setting of control valve 58 to correct for any difference.

As indicated above, in one preferred embodiment, a pump 56 may be utilized as the pressure source instead of a "clean air" source. In such case, the concentration and flow rate of the constituents in that air would have to be determined and subtracted out of the total mass measured during the test. Similarly, in another preferred embodiment adapted for use in analyzing flexible fueled vehicles, i.e. methanol or ethanol blend fueled vehicles, an impinger 60 may further be attached to the inlet 62 of vacuum source 54. Impinger 60 is provided to trap all of the alcohol in the air drawn out of test chamber 52. Two impingers may be used to ensure 100% alcohol absorption. As those skilled in the art will recognize, an impinger is a water bath that fluid (generally air) is bubbled through to expose the fluid to water. Because alcohol has a higher affinity for water than air, applicants have found that any alcohol present in the air drawn out of test chamber 52 is dissolved accordingly. Thus, the mass of alcohol lost during expansion of the test chamber air may be determined in cooperation with a Gas Chromatograph (GC) as described more thoroughly below.

Still referring to FIG. 2, there is further provided controller 64 in electrical communication with volume compensation processor 70 and flow metering device 48 via a feedback loop. In turn, processor 70 is in electrical communication with an externally disposed pressure sensor and an internally disposed temperature sensor 66 and 68, respectively. Finally, there is provided sample and lost mass processor 72 in electrical communication with a fluid analyzer 74, temperature sensor 62, and an internally disposed pressure sensor 76 for determining the emission sample mass and loss calculation. As described more fully below, fluid analyzer 74 may comprise, for example, a continuously operated Flame Ionization Detector (FID), a Fourier Transform Infrared analyzer (FTIR), or any other suitable fluid analyzer. These analyzers are used to determine the amount of evaporative emissions present in the test chamber 52 at discrete times during the test or continuously throughout the test. In operation the sample is drawn into fluid analyzer 74, analyzed and returned to test chamber 52. Processor 72 determines the sample mass and lost mass during the test. In keeping with the invention, those skilled in the art will recognize that if an FTIR is selected as the fluid analyzer, PPM HC and PPM alcohol as well as any other constituent present in air may be determined. A plurality of impingers may also be used in conjunction with fluid analyzer 74 when testing flexible fueled vehicles.

With reference still to FIG. 2, in one preferred embodiment, the control system of the present invention further includes an internally disposed heat exchanger 78 and a desiccant filter/dryer 80. Heat exchanger 78 is used to ensure that any fluid that passes the flow metering device 48 is at the same temperature as the fluid in the rest of test chamber 52. It should be noted, however, that in an alternative embodiment, a temperature correction can be made to obviate the need for a heat exchanger. In such cases, it is recognized that a mass flow metering device must of course be substituted for the flow metering device 48 referenced above. Still further, in yet another alternative embodiment adapted for use in measuring flex fuels, there is further provided a quick disconnects 62 and 63 for replacing impinger 60. As explained in further detail below, for each flex fuel test, there must actually be three (3) impingement samples. The first sample would be to determine the background alcohol level present at the beginning of the test. Similarly, the second sample would be taken with a "large impinger" to determine the alcohol removed from test chamber 52 during the test due to the expansion of air. Finally, the third sample would be taken to determine the mass of constituents being measured at the end of the test. The difference between the determined masses of samples 1 and 3 summed with the determined mass of sample 2 yields the total mass emitted from the vehicle.

Figure 3:
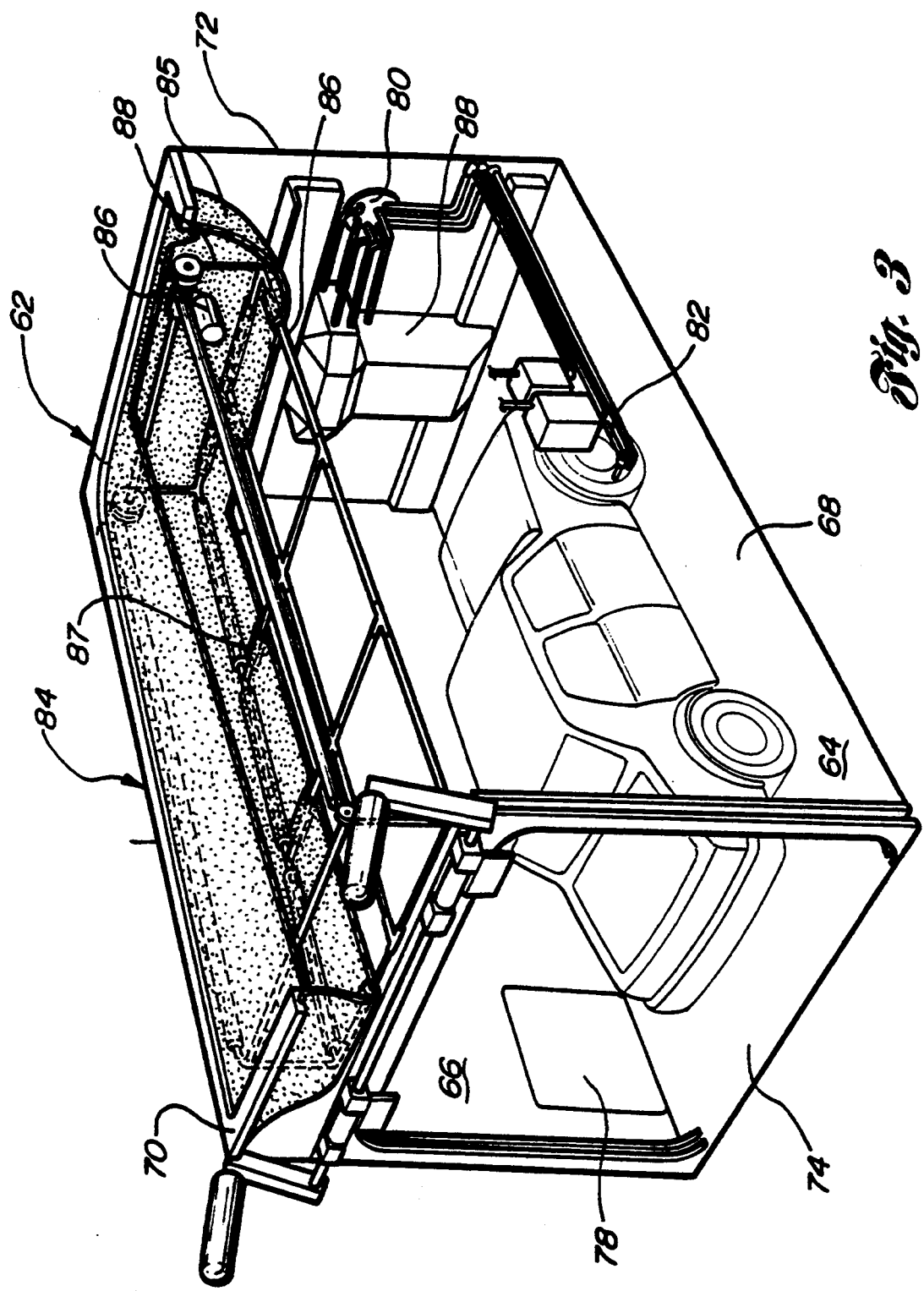
FIG. 3 is a perspective view of an apparatus incorporating the control system of the present invention.

With reference now to FIG. 3, a sealed housing defining a fixed-volume test chamber and incorporating the control system of the present invention is shown generally designated by reference numeral 82. Like prior art SHED 10, SHED 82 is also preferably rectangular in shape and includes a bottom portion 84, side portions 86 and 88, top portion 90 and rear portion 92. SHED 82 further includes a vehicle entrance/exit door 94, an operator egress door 96 and a plurality of penetrations 98 which are provided for sample ports, temperature probes such as RTD 100, and the like. SHED 82 further includes volume compensation means which comprise flow metering devices (not shown) of the type referenced in FIG. 2 and control means (not shown) such as a feedback control circuit incorporating a PID control loop. In operation, as the test chamber fluid expands, fluid ($V_n$) will be evacuated from the test chamber, as determined in accordance with the ideal gas law (PV=nRT). This fluid volume $V_n$ contains a mass of emission sample ($M_n$), which may similarly be determined as described more thoroughly below. By summing the total determined masses ($M_n$) of evaporative emissions evacuated during expansion of the test chamber fluid, a loss calculation will be provided so as to determine the total mass of evaporative emissions at the end of the test.

Significantly, the control system of the present invention is directed for use in a fixed-volume test chamber and thus obviates the need for an internal volume compensation device such as the wall-mounted inflatable bags of the prior art. In operation, test chamber fluid is allowed to escape and the mass of evaporative emissions contained therein is calculated as a loss factor. The disclosed control system is truly leak-tolerant as it does not rely on differential pressure feedback for volume control.

METHOD OF OPERATION

Figure 4:
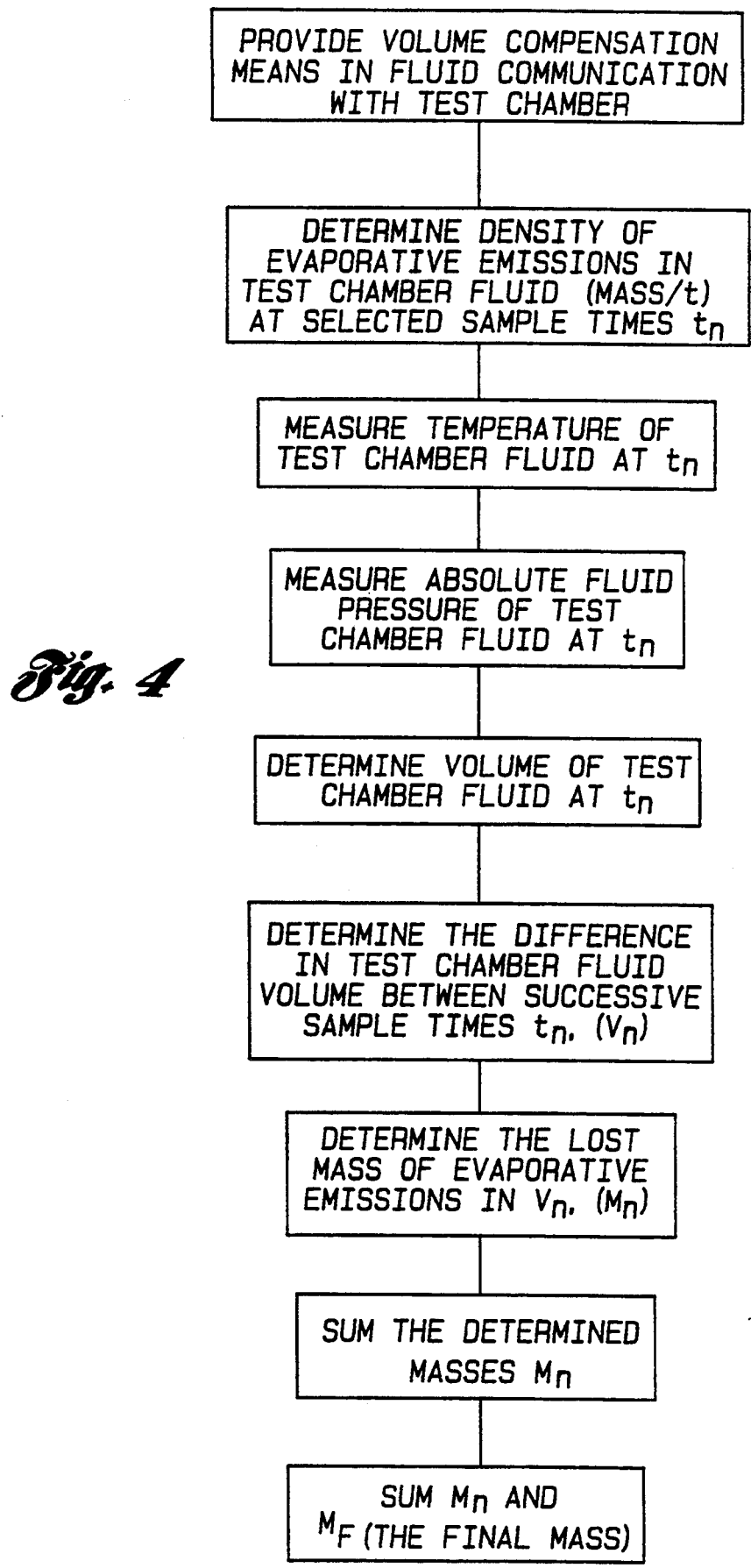
FIG. 4 is a block diagram of the method steps of one preferred embodiment of the present invention.

Referring now to FIG. 4, the method of operation of the control system of the present invention will be described in further detail. As shown in FIG. 4, for each reading (discrete time interval or continuous integration), the absolute fluid pressure of the test chamber must be determined along with the test chamber temperature and the background concentration of the evaporative emissions sought to be measured. In the case of hydrocarbon emissions, those skilled in the art will recognize that hydrocarbon mass may be determined in accordance with the following formula:

$$MHC = kV\,0.0001\,(3)\left[\frac{(CHC_t P_t)}{T_t} - \frac{(CHC_i P_i)}{T_i}\right]$$

where,
MHC=Hydrocarbon mass (gm)
CHC=Hydrocarbon concentration (PPM carbon)
V=Fixed enclosure volume (Ft$^3$)
P=Barometric pressure (in Hg)
T=Enclosure air temperature (R)
k=3.05 English units
i=Initial reading
t=Reading at time (t).

Where the HC concentration is determined using a Flame Ionization Detector (FID), Fourier Transform Infrared Analyzer (FTIR) or other suitable means. In the case of an FID analyzer, for example, the sample pump is adapted to draw sample out of the test chamber 52, pass a small portion of the sample through the flame and return the sample back to the test chamber. The FID output is normally proportional to PPM (Parts Per Million parts of air) HC. The results from this calculation yields mass of hydrocarbon in the test chamber 52 at any point in time not including lost mass due to expansion. Thereafter, the density at a selected sample time may be calculated in accordance with the formula:

$$\rho_t = MHC_t/V_t = \text{Density (gm/ft}^3\text{)}.$$

Once determined, correction of the data for positive changes in volume must then be made using the Ideal Gas Law:

$$\Delta V_t = \frac{V_i P_{(t-1)} T_t}{T_{t-1} P_t} - V_i$$

where,
$\Delta V_t$=Change in volume at time (t) (Ft$^3$)
$V_i$=Initial fixed volume of SHED minus vehicle (Ft$^3$)
$P_{t-1}$=Pressure at previous reading (in Hg)
$P_t$=Pressure at time (t) (in Hg)
$T_t$=Temperature at time t (R)
$T_{t-1}$=Temperature at previous reading (R)

It should be understood that the volume compensation processor of the present invention has been designed based on the understanding that fluid of known mass, temperature, pressure and volume will expand and contract predictably in accordance with the Ideal Gas Law (PV-nRT). Thus, the processor has been designed to compare the mass flow, volumetric flow, total mass or total volume of test chamber fluid present at selected sample times with the rate or total change in temperature so as to determine the amount of fluid which must be provided to or evacuated from the vehicle test chamber 52 to avoid pressurization.

The volume compensation processor therefore comprises a feedback compared to a set point corresponding to the determined volume, mass or rate of fluid flow in volume or mass per unit time at a first selected sample time $t_n$, where n is a positive integer. This set point is compared with volume, temperature and pressure feedback from sample time $t_n$ and a previous selected sample time $t_{n-y}$, where y is a positive integer, through the use of a PID control loop so as to determine the required amount of fluid to be provided to or evacuated from the vehicle test chamber 52 to avoid pressurization. This feedback is received from internally disposed temperature sensor 68 which is in thermal communication with the test chamber 52 and at least one pressure sensor 66 disposed outside of the test chamber.

In one preferred embodiment, the volume compensation process includes the steps of comparing the total volume or mass of fluid present in the vehicle test chamber to the total change in temperature and pressure so as to predictively determine the required volume to be provided to or evacuated from test chamber 52 in accordance with the Ideal Gas Law (PV=nRT), where,
P=pressure,
V=volume,
n=molecular weight,
R=universal gas constant, and
T=temperature.

As those skilled in the art will recognize, between sample times $t_o$ and $t_n$, where n is a positive integer, the change in volume can be predictively determined in accordance with the formula:

$$\frac{P_0 V_0}{T_0} = \frac{P_n P_n}{T_n}.$$

Solving for $V_n$ yields:

$$V_n = \frac{T_n P_o V_o}{T_o P_n}$$

The change in test chamber fluid volume $V_n - V_o$ may be further designated $\Delta V_{sp}$. This value $\Delta V_{sp}$ may be provided as a set point in the PID control loop of controller 64 wherein feedback is provided and compared to the determined total fluid volume which has been provided to or evacuated from the test chamber between sample times $t_o$ and $t_n$ ($\Delta V_{total}$). It should be noted that $\Delta V_{total}$ is measured through the use of flow metering device 48, the output of which is integrated over time. Once determined, this volume difference, ($V_d$), $\Delta V_{sp} - \Delta V_{total}$ may be provided to or evacuated from the test chamber 52 so as to compensate for the decrease or increase in volume of the test chamber fluid.

Still further, in an alternative embodiment, a volume compensation process may be utilized wherein the step of determining the total volume of fluid which has been provided to or evacuated from the test chamber between times $t_o$ and $t_n$, ($\Delta V_{total}$) includes the initial step of measuring the mass flow of fluid which is being provided to or evacuated from the test chamber at time $t_n$, (m). Utilizing an adaption of the Ideal Gas Law (PV=mRT), where R is the specific gas constant, this total mass may thereafter be converted to $\Delta V_{total}$. As those skilled in the art will recognize $$\overline{R} = R/M$$

where M is the molecular weight of the gas.

In yet another alternative embodiment, a volume compensation process may be utilized which, instead of determining and comparing the total volume or mass of fluid provided to or evacuated from test chamber 52, compares the volumetric or mass flow to the rate of temperature and pressure change. Like the control approaches referred above, this embodiment also assumes that the mass, volume, temperature and pressure of the test chamber fluid has been measured or predetermined at a first selected sample time, here $t_{(n-y)}$, where n and y are both positive integers.

At a second selected sample time $t_n$, the temperature of the test chamber fluid and the absolute fluid pressure outside of the test chamber are measured. Again, provided with this information, the volume of the test chamber fluid at sample time $t_n$ ($V_{new}$) may be predictably determined in accordance with the Ideal Gas Law (PV=nRT). This volume, $V_{new}$, must then be compared to the determined volume of the test chamber fluid at sample time $t_n$ to determine the volume difference therebetween ($V_d$). Once determined, $V_d$ may be divided by the elapsed time between sample times $t_n$ and $t_{(n-y)}$. As those skilled in the art will recognize, this calculation will yield the determined rate at which fluid should be provided to or evacuated from the test chamber 52 at sample time $t_n$ in volume per unit time. This value may then be compared to the determined rate at which fluid is provided to or evacuated from the volume compensation means at sample time $t_{(n-y)}$ (volume per unit time) to yield a determined rate difference $R_d$. By increasing or decreasing the rate of flow of fluid by $R_d$, the test chamber volume will be decreased or increased accordingly so as to avoid pressurization.

Still further, in yet another alternative embodiment, it is recognized that the step of determining the rate at which fluid is provided to or evacuated from test chamber 52 at sample time $t_n$ may further include the step of determining the rate at which fluid is provided to test chamber 52 at sample time $t_n$ (in mass per unit time, m). Once determined, this rate may be converted to a corresponding rate in volume per unit time in accordance with an adaption of the Ideal Gas Law (PV=mRT) as referenced above.

The volumetric processing steps disclosed above are more thoroughly described in co-pending U.S. patent application Ser. No. 08/023,322, filed Feb. 26, 1993, which is commonly owned. The disclosure of Ser. No. 08/023,322 is expressly incorporated herein by reference.

As indicated above, an FTIR analyzer may also be used in place of an FID analyzer. In such case, HC as well as methanol and/or ethanol concentrations of alternative fuels may be determined in much the same way with an FID analyzer. In operation, the sample is again drawn from test chamber D2 continuously during the test. Because the FTIR analyzer may be used to determine both HC and alcohol emissions, it is recognized that the analyzer must be set up initially to indicate the total concentration of the evaporative constituent which is of interest. For example, in the case of flexible fueled vehicles, the total HC and total methanol or ethanol concentration would be of interest. Therefore, these measurements should be read and indicated by the analyzer in units of PPM. Significantly, the calculations for alcohol blend fuels are the same as those used for standard fuels except for the constant k. In operation, the system is designed to convert the PPM into density in mass per unit volume mixture, account for lost volume and multiply the same by the density resulting in lost mass. The lost mass in integrated over the test duration and a final total mass is calculated. This lost mass added to the evaporative emissions mass left in test chamber 52 at the end of the test as indicated by the last concentration sample yields the total evaporative emission from the vehicle during the test.

As indicated above, in an alternative embodiment, alcohol emissions may also be determined through the use of a plurality of impingers. In this method, at the beginning of the test, a sample of the concentration of alcohol in test chamber 52 is taken and passed through a first impinger 60 at a selected flow rate for a selected amount of time. Thereafter, the first impinger 60 is removed and a second "large impinger" (not shown) is connected in its place. This "large impinger" remains attached to test chamber 52 via outlet 62 of the volume compensation device. In operation, air removed from test chamber 52 passes through the large impinger which traps any alcohols present in the impinger water. This effectively continuously integrates the lost mass of alcohol over the entire test much like the calculations for the FID approach. In keeping with the invention, during contraction of the test chamber air, air is passed into test chamber 52 bypassing the impinger since no sample is lost during these cycles. At the end of the test, the large impinger is removed and a third impinger (not shown) is put in its place. Again, a sample is drawn from the test chamber 52 for a specific amount of time and flow rate. This sample, when analyzed, will indicate the concentration of alcohol in the test chamber left at the end of the test. As referenced above, the concentration found at the beginning of the test is then subtracted from the concentration at the end of the test. Thereafter, the mass of the alcohols emitted is calculated. This mass emitted added to the lost mass trapped in the large impinger will yield the total evaporated alcohol emissions during the test.

Significantly, the impinger samples are analyzed using a Gas Chromatograph (GC). As those skilled in the art will recognize, a Gas Chromatograph is not a continuous sampling system. Thus the samples must be taken and analyzed separately to determine the mass of alcohol per unit sample mass. In operation, the GC will determine the entire chemical breakdown of the mass of each constituent dissolved in the fluid which is sought to be analyzed. For example, a 15 ml impinger may be used to analyze a 0.5 ml sample of water in cooperation with a GC. If the sample contained 0.01 mg of alcohol, it is recognized that 0.3 mg of alcohol will be present in the impinger. (0.1 mg alcohol *15 ml=0.3 mg alcohol). In accordance with the invention, if the 15 ml impinger reference above was the second or "large impinger", then the 0.3 mg alcohol would account for all of the alcohol lost from the test chamber during the test. Similarly, if the 15 ml impinger was used at the end of the test, then the determined mass of alcohol would have to be divided by the total volume of air drawn into the impinger. For example, consider an impinger which has had 0.2 CFM of air passed through it during an 1800 second time period (6 cubic feet of air). If it is determined that 0.3 mg of alcohol are present in the impinger at the end of the test, then there must be 0.3 mg of alcohol per 6 cubic feet of test chamber air. If the test chamber has a volume of 1500 cubic feet, then 75 mg of alcohol must have been present in the test chamber at the end of the test.

While the best modes for carrying out the invention have been described in detail, those familiar with the art to which this invention relates will recognize various alternative designs and embodiments for practicing the invention as defined by the following claims.

What is claimed is:

1. A leak-tolerant method of measuring evaporative emissions from motor vehicles in accordance with prescribed fluid temperature profiles in a fixed volume test chamber filled with a fluid having a predetermined mass, volume, temperature and pressure at time $t_o$ and a determined mass at a final reading $t_f$, ($M_f$), comprising the steps of:

providing volume compensation means in fluid communication with said test chamber for compensating for changes in said test chamber fluid volume;

determining the density of said evaporative emissions in said test chamber fluid in mass per unit volume at selected sample times $t_n$, where n is a positive integer;

measuring the temperature of said test chamber fluid at said sample times $t_n$;

measuring the absolute fluid pressure of said test chamber at said sample times $t_n$;

determining the volume of said test chamber fluid at said sample times $t_n$ in accordance with the Ideal Gas Law ($PV=nRT$);

determining the difference in said test chamber fluid volume between successive sample times $t_n$, (Vn);

determining the lost mass of said evaporative emissions in Vn, ($M_n$);

summing the determined masses of said evaporative emissions ($M_n$) to provide a calculation of the total evaporative emissions lost by said volume compensation means during expansion of said test chamber fluid, ($M_{loss}$); and summing $M_{loss}$ and $M_f$.

2. A leak-tolerant method of measuring alcohol emissions from motor vehicles in accordance with prescribed fluid temperature profiles in a fixed volume test chamber, comprising the steps of:

providing flow metering means in fluid communication with said test chamber for compensating for changes in said test chamber fluid volume;

providing a first, second and third impinger, each adapted to be removably connected to said flow metering means;

passing a sample of said test chamber fluid through said first impinger at a first selected rate of flow for a first selected period of time to determine the initial concentration of alcohol in said test chamber fluid;

replacing said first impinger with said second impinger for the duration of said temperature profiles to determine the mass of alcohols lost during said temperature profiles;

replacing said second impinger with said third impinger and passing a sample of said test chamber fluid therethrough at a second selected rate of flow for a second selected period of time to determine the final concentration of alcohol in said test chamber fluid;

determining the difference between said initial and final alcohol concentrations, determining the mass of said determined alcohol concentration difference; and summing said determined mass of said alcohol concentration difference with said mass of alcohols lost during said temperature profiles.

* * * * *

UNITED STATES PATENT AND TRADEMARK OFFICE
CERTIFICATE OF CORRECTION

PATENT NO. : 5,369,976
DATED : December 6, 1994
INVENTOR(S) : Ratton

It is certified that error appears in the above-indentified patent and that said Letters Patent is hereby corrected as shown below:

Column 1, line 9, delete ";" after "this".
Column 1, line 31, delete "86,101" and insert therefor --86.101--.
Column 1, line 39, delete "86,078-3" and insert therefor --86.078-3--.
Column 2, line 22, delete "Loss" and insert therefor --loss--.
Column 7, line 40, delete "$\frac{P_n P_n}{T_n}$" and insert therefor --$\frac{P_n V_n}{T_n}$--.

Signed and Sealed this

Twenty-sixth Day of December, 1995

Attest:

BRUCE LEHMAN

*Attesting Officer*     *Commissioner of Patents and Trademarks*